US00PP18310P2

(12) United States Plant Patent
Heinz

(10) Patent No.: US PP18,310 P2
(45) Date of Patent: Dec. 11, 2007

(54) ***MYOSOTIS* PLANT NAMED 'BABY BLUE'**

(50) Latin Name: ***Myosotis palustris*×*Myosotis sylvativa***
Varietal Denomination: Baby Blue

(75) Inventor: Markl Heinz, Tuntenhausen (DE)

(73) Assignee: InnovaPlant GmbH + Co. KG, Gensingen (DE)

( * ) Notice: Subject to any disclaimer, the term of this patent is extended or adjusted under 35 U.S.C. 154(b) by 168 days.

(21) Appl. No.: 11/273,540

(22) Filed: Nov. 14, 2005

(51) Int. Cl.
*A01H 5/00* (2006.01)

(52) U.S. Cl. ..... Plt./263
(58) Field of Classification Search ..... Plt./263
See application file for complete search history.

*Primary Examiner*—Wendy C. Haas
*Assistant Examiner*—Georgia Helmer
(74) *Attorney, Agent, or Firm*—C. A. Whealy

(57) ABSTRACT

A new and distinct cultivar of *Myosotis* plant named 'Baby Blue', characterized by its compact, upright and outwardly spreading plant habit; freely branching growth habit; early flowering habit; and numerous soft blue-colored flowers.

1 Drawing Sheet

Botanical designation: *Myosotis palustris*×*Myosotis sylvativa.*
Cultivar denomination: 'Baby Blue'.

BACKGROUND OF THE INVENTION

The present Invention relates to a new and distinct cultivar of *Myosotis* plant, botanically known as *Myosotis palustris*×*Myosotis sylvativa,* and hereinafter referred to by the name 'Baby Blue'.

The new *Myosotis* is a product of a planned breeding program conducted by the Inventor in Tuntenhausen, Germany. The objective of the breeding program was to create new compact pot-type *Myosotis* cultivars with freely branching and early flowering habit.

The new *Myosotis* originated from a cross-pollination made by the Inventor in 1998 of an unnamed selection of *Myosotis palustris,* not patented, as the female, or seed, parent with an unnamed selection of *Myosotis sylvativa,* not patented, as the male, or pollen, parent. The new *Myosotis* was discovered and selected by the Inventor as a flowering plant within the resultant progeny of the stated cross-pollination in a controlled environment in Tuntenhausen, Germany in 1999.

Asexual reproduction of the new *Myosotis* by terminal cuttings in Tuntenhausen, Germany since 1999, has shown that the unique features of this new *Myosotis* are stable and reproduced true to type in successive generations of asexual reproduction.

SUMMARY OF THE INVENTION

The following traits have been repeatedly observed and are determined to be the unique characteristics of 'Baby Blue'. These characteristics in combination distinguish 'Baby Blue' as a new and distinct cultivar:

1. Compact, upright and outwardly spreading plant habit.
2. Freely branching growth habit.
3. Early flowering habit.
4. Numerous soft blue-colored flowers.

Plants of the new *Myosotis* differ from plants of the female parent selection primarily in the following characteristics:

1. Plants of the new *Myosotis* are more uniform in growth habit than plants of the female parent selection.
2. Plants of the new *Myosotis* have shorter leaves than plants of the female parent selection.
3. Plants of the new *Myosotis* have larger flowers than plants of the female parent selection.
4. Plants of the new *Myosotis* flower earlier than plants of the female parent selection.

Plants of the new *Myosotis* differ from plants of the male parent selection primarily in the following characteristics:

1. Plants of the new *Myosotis* are not as upright as plants of the male parent selection.
2. Plants of the new *Myosotis* are less vigorous than plants of the male parent selection.
3. Plants of the new *Myosotis* are more freely branching than plants of the male parent selection.
4. Plants of the new *Myosotis* have darker green-colored leaves than plants of the male parent selection.

Plants of the new *Myosotis* can be compared to plants of the *Myosotis* cultivar Anne Marie Fischer, not patented. In side-by-side comparisons conducted in Tuntenhausen, Germany, plants of the new *Myosotis* differed from plants of the cultivar Anne Marie Fischer in the following characteristics:

1. Plants of the new *Myosotis* were more compact than plants of the cultivar Anne Marie Fischer.
2. Plants of the new *Myosotis* had larger flowers than plants of the cultivar Anne Marie Fischer.
3. Plants of the new *Myosotis* flowered earlier than plants of the cultivar Anne Marie Fischer.
4. Plants of the new *Myosotis* and the cultivar Anne Marie Fischer differed in flower color as plants of the cultivar Anne Marie Fischer had fainter blue-colored flowers.
5. Flowers of plants of the new *Myosotis* were longer lasting than flowers of plants of the cultivar Anne Marie Fischer.

BRIEF DESCRIPTION OF THE PHOTOGRAPHS

The accompanying colored photographs illustrate the overall appearance of the new *Myosotis,* showing the colors as true as it is reasonably possible to obtain in colored reproductions of this type. Colors in the photographs may differ slightly from the color values cited in the detailed botanical description which accurately describe the colors of the new *Myosotis*.

The photograph at the bottom of the sheet comprises a side perspective view of a typical plant of 'Baby Blue' grown in a container.

The photograph at the top of the sheet is a close-up view of typical flowers of 'Baby Blue'.

DETAILED BOTANICAL DESCRIPTION

The new *Myosotis* has not been observed under all possible environmental conditions. The phenotype may vary somewhat with variations in environment such as temperature and light intensity, without, however, any variance in genotype.

The aforementioned photographs, following observations and measurements describe plants grown in Bonsall, Calif. in an outdoor nursery during the spring and summer under commercial production practices. Plants were about four weeks from planting rooted young plants when the photographs and description were taken. During the production of the plants, day temperatures ranged from 10° C. to 32° C. and night temperatures ranged from 4° C. to 21° C. In the following description, color references are made to The Royal Horticultural Society Colour Chart, 1995 Edition, except where general terms of ordinary dictionary significance are used.

Botanical classification: *Myosotis palustris*×*Myosotis sylvativa* cultivar 'Baby Blue'.

Parentage:

*Female, or seed, parent.*—Unnamed selection of *Myosotis palustris,* not patented.

*Male, or pollen, parent.*—Unnamed selection of *Myosotis sylvativa,* not patented.

Propagation:

*Type.*—By cuttings.

*Time to initiate roots, summer.*—About 14 days at 20° C.

*Time to initiate roots, winter.*—About 18 days at 20° C.

*Time to produce a rooted cutting.*—About 20 days at 20° C.

*Root description.*—Fine, white in color.

*Rooting habit.*—Freely branching.

Plant description:

*Plant form.*—Compact, upright to somewhat outwardly spreading deciduous perennial.

*Growth habit.*—Moderately vigorous. Freely branching, about ten lateral branches develop per plant.

*Plant height.*—About 13 cm.

*Plant width* (*spread*).—About 23 cm.

*Lateral branches.*—Length: About 8.5 cm. Diameter: About 3 mm. Internode length: About 1 cm. Strength: Strong. Texture: Pubescent. Color: 200B.

*Foliage description.*—Arrangement: Alternate, simple. Length: About 4 cm. Width: About 1.7 cm. Shape: Oblanceolate. Apex: Acute. Base: Attenuate. Margin: Entire. Texture, upper and lower surfaces: Pubescent; rough, coarse. Venation pattern: Pinnate; arcuate. Color: Developing leaves, upper and lower surfaces: 146A. Fully expanded leaves, upper surface: 147A; venation, 147B. Fully expanded leaves, lower surface: 147B; venation, 147C. Petiole length: About 1.2 cm. Petiole diameter: About 5 mm. Petiole texture, upper and lower surfaces: Pubescent. Petiole color, upper and lower surfaces: 146B.

Flower description:

*Flower type/habit.*—Single, rounded salverform flowers arranged in axillary cymes; flowers face upright and outward. Freely flowering habit with about 200 flower buds and flowers per inflorescence. Flowers not fragrant.

*Natural flowering season.*—Continuously flowering from March through May in Southern California. Flowers not persistent.

*Postproduction longevity.*—Flowers last about one week on the plant.

*Inflorescence height.*—About 5.5 cm.

*Inflorescence diameter.*—About 2 cm.

*Flower buds.*—Height: About 6 mm. Diameter: About 3 mm. Shape: Ovoid. Color: 75A.

*Flowers.*—Diameter: About 1.2 cm. Depth: About 5 mm.

*Petals.*—Quantity per flower: Typically five in a single whorl; petals fused at the base into a tube. Lobe length: About 6 mm. Lobe width: About 5 mm. Lobe shape: Spatulate. Apex: Rounded. Margin: Entire. Texture, upper and lower surfaces: Smooth, glabrous. Color: Developing petals, upper surface: 97D; towards the base, 155D; ring at throat, 63B. Developing petals, lower surface: 85B. Fully expanded petals, upper surface: 100B; towards the base, 155D; ring at throat, 12A; color becoming closer to 101C with development. Fully expanded petals, lower surface: 100C.

*Sepals.*—Quantity per flower: Typically five in a single whorl, fused; companulate calyx. Length: About 2 mm. Width: About 1 mm. Shape: Lanceolate. Apex: Acute. Texture, upper and lower surfaces: Pubescent. Color, upper and lower surfaces: 146A.

*Peduncles.*—Length: About 2.2 cm. Diameter: About 1 mm. Aspect: About 45° C. from the stem axis. Strength: Strong. Texture: Pubescent. Color: 146A.

*Pedicels.*—Length: About 6 mm. Diameter: Less than 1 mm. Aspect: About 30° C. from peduncle axis. Strength: Strong. Texture: Pubescent. Color: 146A.

*Reproductive organs.*—Stamens: Quantity per flower: Typically five; fused with petals in tube. Anther shape: Oval. Anther length: Less than 1 mm. Anther color: 12A. Pollen amount: Scarce. Pollen color: 12A. Pistils: Quantity per flower: Typically one. Pistil length: About 2 mm. Stigma shape: Rounded. Stigma color: 157A. Style length: About 1 mm. Style color: 157A. Ovary color: 144A.

*Seed/fruit.*—Seed and fruit development have not been observed.

Disease/pest resistance: Plants of the new *Myosotis* have not been observed to be resistant to pathogens and pests common to *Myosotis*.

Temperature tolerance: Plants of the new *Myosotis* have been observed to tolerate high temperatures of 40° C. and are hardy to USDA Zone 8.

It is claimed:

1. A new and distinct cultivar of *Myosotis* plant named 'Baby Blue', as illustrated and described.

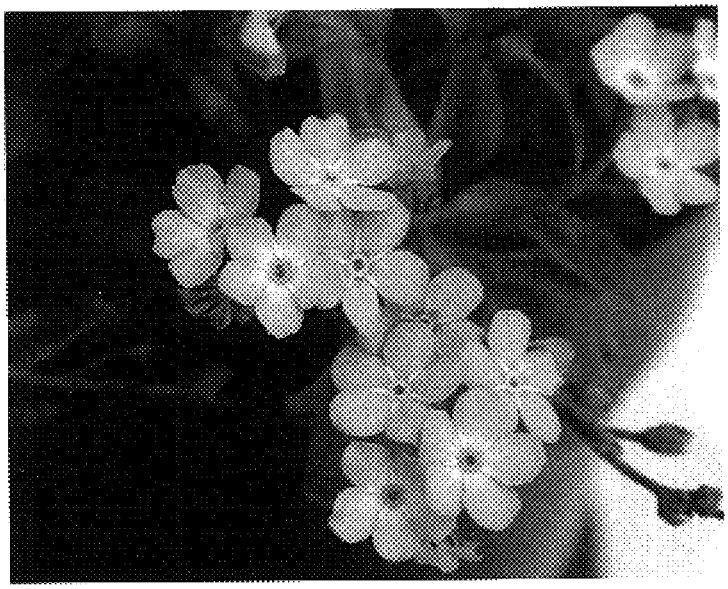
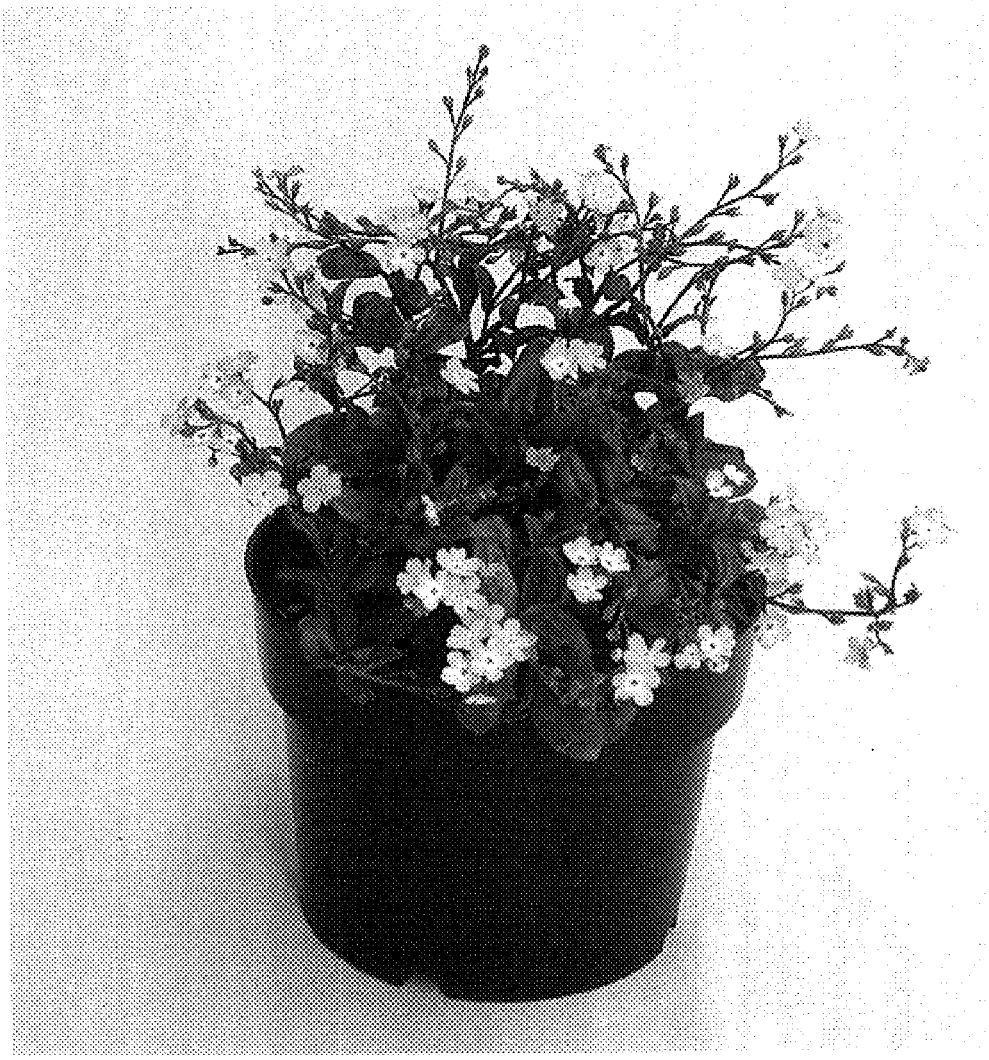

* * * * *